United States Patent [19]
Brown

[11] Patent Number: 6,086,594
[45] Date of Patent: Jul. 11, 2000

[54] CEMENT PRESSURIZING DEVICE

[76] Inventor: Byron L. Brown, 2315 Hendricks Blvd., Fort Smith, Ark. 72903

[21] Appl. No.: 09/173,906

[22] Filed: Oct. 16, 1998

[51] Int. Cl.$^7$ .................................................... A61B 17/58
[52] U.S. Cl. .............................................................. 606/92
[58] Field of Search ................................ 606/94, 92, 93, 606/91; 623/23; 222/391

[56] References Cited

U.S. PATENT DOCUMENTS

| | | | |
|---|---|---|---|
| 4,357,716 | 11/1982 | Brown | 3/1.913 |
| 4,405,249 | 9/1983 | Scales | 606/93 |
| 4,546,767 | 10/1985 | Smith | 606/92 |
| 4,966,601 | 10/1990 | Draenert | 606/92 |
| 4,994,065 | 2/1991 | Gibbs et al. | 606/92 |
| 5,047,061 | 9/1991 | Brown | 623/23 |

OTHER PUBLICATIONS

Brochure or Leaflet entitled "Miller™ Bone Cement Injector", Zimmer 1989, 1981.
1–page The Zimmer Bone Cement System—Meeting the needs of the surgeon (undated).
1–page "Surgical Simplex P Bone Cement . . . The Dependable One", Howmedica (undated).

*Primary Examiner*—Michael Buiz
*Assistant Examiner*—Tan-Uyen T. Ho
*Attorney, Agent, or Firm*—Jones, Day, Reavis & Pogue

[57] ABSTRACT

Apparatus and method for forcing flowable cement out of a container into a bone cavity under pressure for binding a prosthesis in the bone cavity with minimal bubbles and voids. The apparatus includes a first pressurization device such as a ratchet gun for forcing the flowable cement from a container of cement into the bone cavity in first increments. A second pressurization device then forces the flowable cement out of the container into the bone cavity in second increments smaller than the first increments to control the pressure in the bone cavity by causing it to increase in smaller increments than with the first pressurization device.

20 Claims, 2 Drawing Sheets

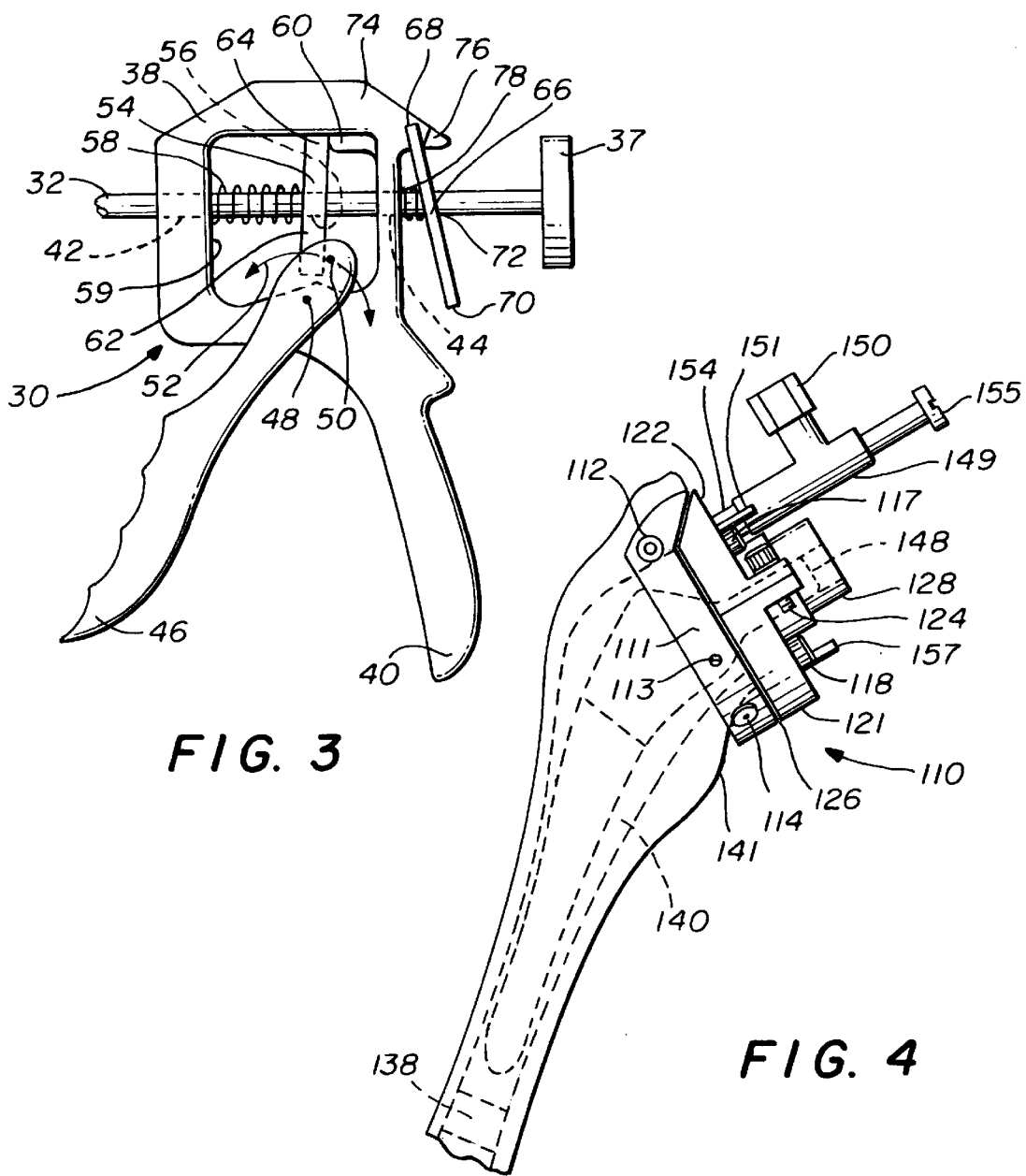
FIG. 3
FIG. 4
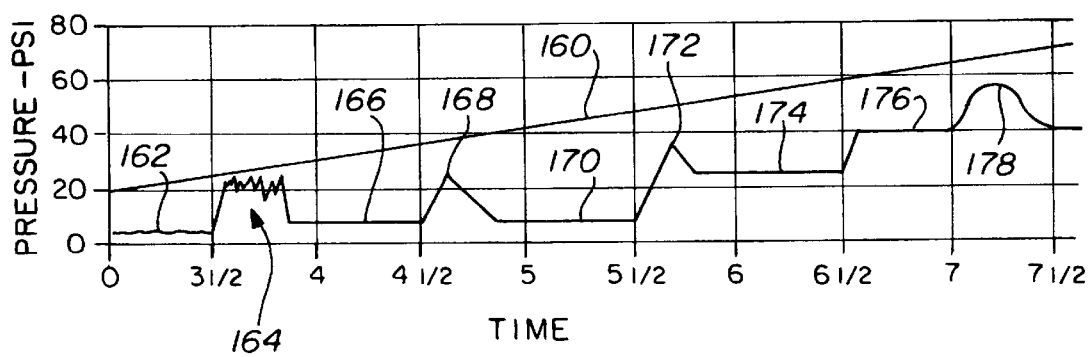
FIG. 5

CEMENT PRESSURIZING DEVICE

BACKGROUND OF THE INVENTION

1. Field of the Invention

The present invention relates in general to the cementing of a prosthesis in a bone cavity and specifically to apparatus for use with a source of bone cement having a movable piston for supplying the cement under pressure to a bone cavity. The attachment enables a user to supply the cement to the bone cavity in controllable and exact small quantities and consequently increase pressure in more precise increments than is possible by use of presently available devices.

2. Description of Related Art Including Information Disclosed Under 37 CFR 1.97 and 1.98

Commonly owned U.S. Pat. No. 4,357,716 and copending application Ser. No. 09/169,737 now U.S. Pat. No. 5,951,563, entitled "Sensor System for Flowable Cement", filed on the same date as this application by the same inventor, are both incorporated in their entirety herein by reference. The U.S. patent discloses a system for mounting a femoral stem prosthesis in the femoral canal with the use of a cement. Copending patent application Ser. No. 09/169,737 now U.S. Pat. No. 5,951,563 discloses a sensor for enabling the viscosity of a flowable cement to be detected as it is pressurized into the bone cavity section so as to prevent the flowable cement from passing through the intertrabecular spaces in the bone wall into the blood stream of the patient.

The process disclosed in U.S. Pat. No. 4,357,716 includes sealing the bone cavity section in a substantially fluid-tight relationship, inserting the cement through a seal into the bone cavity under pressure, having an air escape orifice that allows air and body fluids to escape the bone cavity until it is full of cement, plugging the air escape cavity, and holding the pressure on the cement until it sets. Another method of pressurizing bone cement in a bone cavity consists of partially filling the cavity with cement then, using a cannulated plastic or rubber plug at the end of the bone cavity, inserting the nozzle of the cement syringe through the plug, and adding cement and pressure for a period of approximately 20 seconds. Such pressurization is done at approximately 4 minutes from beginning to mix at a time when the cement is of low viscosity. The pressure which is applied is that amount that "feels right". The plug and syringe are then removed and the prosthesis inserted into the cavity.

Yet another method of pressurizing cavities with cement is to use orifices in the prosthesis itself to inject the cement under pressure.

Presently, the major compounds of bone-cement consist of a liquid monomer of methylmethacrylate, a powder, polymethacrylate, and radiopaque barium sulfate. The liquid and powder may be mixed by one of several methods and then deposited into a gun or syringe having a long nozzle. The cement is injected in a retrograde fashion, i.e. from the bottom up to near the top of the femoral canal. The initial injection of cement is somewhat timely. It should begin when the mixture is in the early doughy state. The cement should be of such viscosity that the femoral canal can be satisfactorily filled without entrapment, or at least with minimal entrapment, 1of air pockets. At the same time, the cement should be of such viscosity that it will partially fill the intertrabecular spaces but not flow from the intertrabecular spaces into the veins beyond the cortical bone. Usually the mixture changes from a liquid state to an early doughy state at about three minutes from beginning to mix the liquid monomer and the powder polymer.

The change from the stage when the mixture is a liquid to a slightly doughy state usually occurs in a matter of a few seconds. That period of time varies somewhat with different brands of cement. Other factors also influence the speed of this reaction or change. A variation of six degrees temperature markedly alters the speed of the reaction. A higher temperature increases the speed. Therefore, the room temperature, the overhead operating room lights, the temperature of the vial and monomer, the temperature of the package powder and the mixing bowl and the stirring ladle all influence the speed of the reaction.

Further, the method and seed of mixing affect the speed of the reaction. The greater the amount of oxygen that is mixed with the cement the more the speed of the reaction will be decreased. Most mixing is done in a container with a vacuum attached to help remove ambient vapor from the operating room. The vacuum pulls air into the mixing bowl and so the length of time that the vacuum is attached and the amount of suction influences the amount of oxygen that will pass over the mixture as well as the degree of evaporation. Further, the monomer-polymer ratio may also have been altered which affects the speed of the reaction.

The fact is, it is extremely important for the physician to monitor the viscosity of the cement so that, when it is still in a highly liquid state, it will not be forced under pressure through the intertrabecular spaces to the veins lying beyond the cortical wall.

A method of pressurizing cement in the femoral canal or other bone cavity is that of inserting the prosthesis through a sealing device and inserting it in the femoral canal and attaching the sealing device to the canal or bone cavity in a substantially fluid-tight relationship and injecting cement through orifices in the sealing device. This is clearly shown in commonly owned U.S. Pat. No. 4,357,716. The sealing device in U.S. Pat. No. 4,357,716 includes an orifice for venting the canal so that air and other bodily fluids in the femoral canal can be displaced by the cement and escape through the orifice. However, when cement begins to exude from the orifice, it is then closed so that cement can no longer exude and the pressure is increased to compress the cement in an effort to remove and compress air bubbles and to cause the cement to fill the intertrabecular spaces and surround the prosthesis in a binding relationship. The hole from which the cement can exude is a one-quarter inch hole which, of course, allows the fluid products to easily flow therethrough.

Thus, when the orifice is sealed and pressure is applied, if the cement does not have sufficient viscosity, the pressure applied may force it through the intertrabecular spaces and Haversian canals and into the veins on the other side of the cortical wall.

If cement does flow into the veins on the other side of the cortical wall, there may be extremely adverse effects on the patient's health.

Copending application Ser. No. 09/169,737 now U.S. Pat. No. 5,951,563 discloses novel apparatus and methods to monitor the viscosity of the cement to which pressure is being applied so that pressure of greater amounts than are needed or desired will not be applied when the viscosity is low and so that a maximal amount of pressure can be applied when the viscosity has increased to the point it cannot flow through the intertrabecular spaces and into the circulation beyond the bone.

It is also extremely important that the user be able to selectively increase the pressure at which the cement is introduced into the bone cavity as the viscosity increases, to assure that the cement is not inadvertently forced through the intertrabecular spaces of the bone.

Thus, it would be desirable to have a more exact and controlled way of incrementally increasing the pressure applied to the cement as the viscosity of the cement increases.

SUMMARY OF THE INVENTION

The apparatus of the present invention allows a user to precisely control the amount of cement injected into a bone cavity and thereby selectively increase the pressure of the cement in the bone cavity by small and precise increments. It is particularly useful for cementing a prosthesis in a bone cavity having a cortical wall with intertrabecular spaces. The capability of increasing the pressure applied to the cement allows the physician or user to avoid applying excessive pressure to the cement and thereby avoid forcing the cement through the intertrabecular spaces.

The apparatus of the invention cooperates with a cement container or source, such as a syringe device, or a ratchet gun with a cartridge having a piston for ejecting cement from the container. A piston or plunger rod engages the piston of the cement container or cartridge to apply pressure and eject the cement. Typically, the plunger rod and consequently the piston in the container are moved by applying force directly, such as by use of a ratchet gun, so as to supply a large amount of cement into the bone cavity. Then, according to the present invention, the piston of the cement container is moved forward a small and selected distance to eject the cement in exact amounts and directly increase the pressure of the cement by precise increments. According to one embodiment of the invention, an attachment having a threaded rod with first and second ends is secured to the ratchet gun such that the threaded rod is supported by a nut plate so as to be substantially coaxial with the plunger rod which bears against the piston of the container. A pressure plate connected to the first end of the threaded rod contacts the exposed end of the plunger rod of the ratchet gun and a knob or thumbscrew or the like is secured to the second end such that selected axial rotation of the threaded rod in the nut plate will advance the pressure plate to move the plunger rod of the ratchet gun an exact distance which in turn moves the piston in the container so as to eject a precise amount of cement.

Actual injection of cement into a bone cavity requires the cement to be applied under pressure so as to avoid voids or spaces in the cement and to adequately compact the cement without forcing the cement through the intertrabecular spaces. Since the viscosity of the cement is continually increasing as it cures, it is possible to increase the pressure as the viscosity increases without forcing the cement into the intertrabecular spaces. Therefore, if the viscosity of the cement can be determined, the invention provides a way of increasing (or decreasing) pressure as appropriate for the viscosity of the cement without forcing the cement into the intertrabecular spaces.

Thus, it is an object of the invention to enable a user to pressurize cement in a bone cavity without forcing the cement through the intertrabecular spaces and Haversian canals in the cortical wall.

It is another object of the invention to provide apparatus for ejecting bone cement in precise amounts so as to control the pressure applied to the cement for proper compaction without forcing it through the cortical wall of the bone.

Thus, the present invention discloses an attachment for a ratchet gun having a movable plunger rod that pressurizes cement in a bone cavity. The plunger rod includes a first end which engages the piston in a container of cement, and the ratchet gun includes a pivotal handle which engages and incrementally moves the piston of the container to force the bone cement out of the container into a bone cavity under pressure. The present inventive attachment enables a physician or user to apply the cement under pressure to the bone cavity in a more controlled way and in smaller units of pressure than with the pivotal handle.

BRIEF DESCRIPTION OF THE DRAWINGS

These and other features of the present invention will be more fully disclosed when taken in conjunction with the following Detailed Description of the Preferred Embodiment(s) in which like numerals represent like elements and in which:

FIG. 3 is a partial cross-sectional side view of the piston-advancing mechanism taken along lines 3—3 of FIG. 1;

FIG. 4 is a side elevation view of the cement injection valve of a ceiling plate attached to the bone and prosthesis in condition for receiving a the device of FIG. 1 and injecting cement into the bone cavity; and FIG. 5 is a time pressure graph representative of a typical pressurization cycle of cement in a bone cavity.

DETAILED DESCRIPTION OF THE PREFERRED EMBODIMENT(S)

Figure 1:
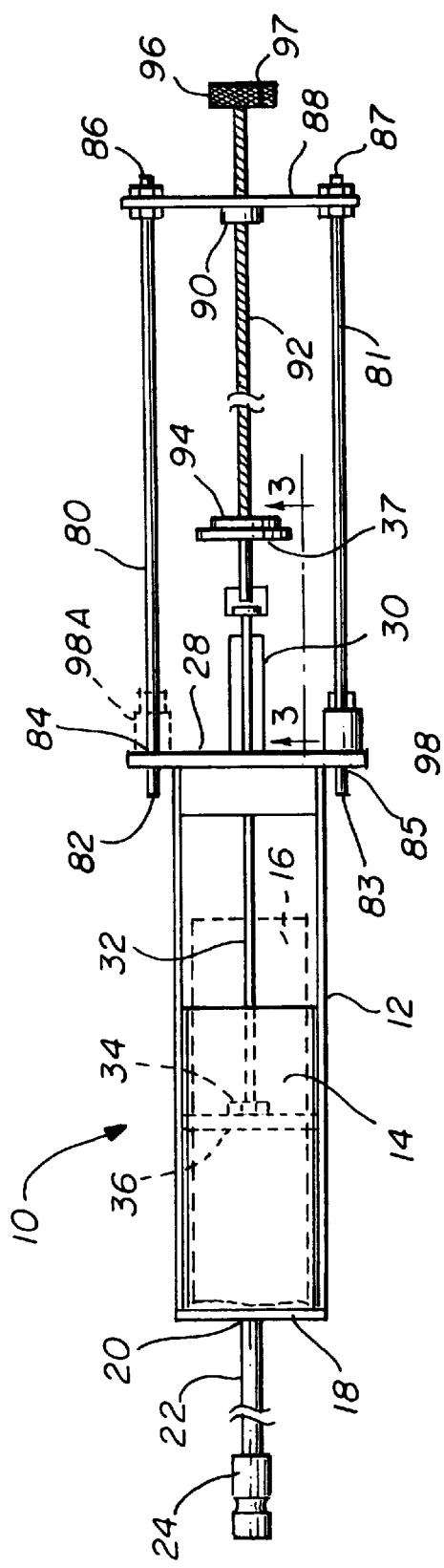
FIG. 1 is a top view of a ratchet gun including one embodiment of apparatus of this invention for supplying bone cement according to the inventive concepts hereof.
Figure 2:
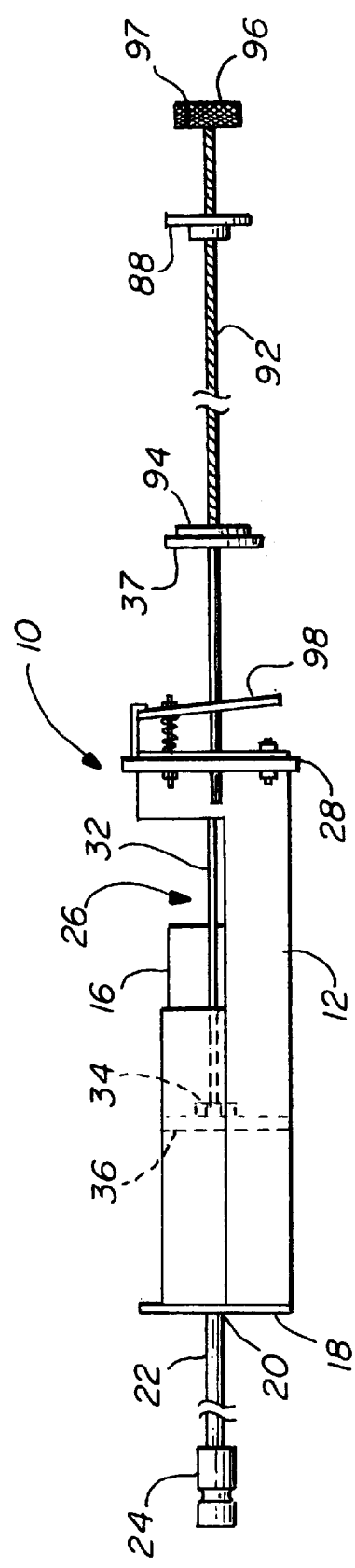
FIG. 2 is a partial side elevation view of the device of FIG. 1.

Referring to FIGS. 1–3, there is shown a cement ratchet gun incorporating the novel concepts of the invention. As shown, the ratchet gun apparatus 10 includes a receiving housing 12 defining a tubular cavity 14 for receiving a cartridge or container 16 (shown in dotted lines). Receiving housing 12 includes a front end 18 having an aperture 20 therethrough such that nozzle 22 of cartridge 16 may pass outside of receiving housing 12. There may also be included a quick-disconnect fitting 24 at the end of nozzle 22. The housing further includes an insertion window 26 which allows a cartridge or cement container 16 to be dropped into the housing. Receiving housing 12 further includes a back wall 28 to which is attached a plunger rod advancing mechanism 30. Plunger rod advancing mechanism 30 is not shown in side view FIG. 2 but is shown in detail in FIG. 3. Plunger rod advancing mechanism 30 provides a means for rapidly advancing plunger rod 32 in a forward direction so as to eject cement in large amounts. Plunger rod 32 extends from a contact pad 34 which bears against the cartridge piston 36 such that axial movement of the contact pad will apply force to the cartridge piston to eject cement from the cartridge 16. As shown, plunger rod 32 extends from the contact pad 34 through the plunger rod advancing mechanism 30 to a pressure pad 37. As shown in more detail in FIG. 3, plunger rod advancing mechanism 30 includes a housing 38 with a handle extension 40. Housing 38 further defines two apertures 42 and 44 having a diameter slightly larger than the diameter of the plunger rod 28 so as to provide a sliding fit. Lever handle 46 is attached to housing 38 by pivot pin 48. Also included on lever handle 46 is a pressure roller or tab 50 that can move in the directions indicated by the double-headed arcuate arrow 52. Plunger rod advancing mechanism 30 further includes a freely floating advancing lever 54 which defines an aperture 56 for providing a sliding fit around plunger rod 32. Coil spring 58 surrounds plunger rod 32 and bears against front face 59 of housing 38 and advancing lever 54 thereby biasing advancing lever 54 against anvil 60 and pressure roller or tab 50. Thus, when lever handle 46 is squeezed, pressure roller 50 moves forward and applies a force to bottom portion 62 of advancing lever 54. However, since the top portion 64 of advancing lever 54 rests against anvil 60, the applied force results in rotational movement of the advancing lever 54 which causes advancing lever 54 to grip the plunger rod 32 and move the rod in a forward direction. When the lever handle 46 is then released, the gripping force is relaxed such that plunger rod 32 may again readily slide through the advancing lever. Thus, the advancing lever returns to its biased position in response to coil spring 58. It will be appreciated, of course, that if there is a resisting pressure on the plunger rod 32, then the plunger rod would move in an opposite direction from that caused by squeezing the hand 46. Therefore, it is necessary that the plunger rod 32 be locked in position after it is moved forward so that the handle can reset and it can then be moved forward again. To accomplish this there is also included in the plunger rod advancing mechanism 30 a locking/quick-release lever 66 having a top portion 68 and a bottom portion 70. In a manner similar to advancing lever 54, the locking/quick-release lever 66 also defines an aperture 72 slightly larger than the diameter of the plunger rod such that a sliding fit is provided. Top portion 68 of locking/quick-release lever 66 defines a yoke (not shown) that straddles top member 74 of plunger rod advancing mechanism 30. Top member 74 further defines a stop tab 76 that prevents the locking/quick-release lever 66 from moving in a rearward direction. A second coil spring 78 biases locking/quick-release lever 66 in a rearward direction thereby causing rotation of the locking/quick-release lever 66 such that the lever grips plunger rod 32 and prevents it from moving rearwardly. However, it will be appreciated that by applying a forward pressure to the bottom portion 70 of locking/quick-release lever 66, the lever will no longer grip plunger rod 32 and the plunger rod can then move in a forward direction. Thus, it will be appreciated at this point that, by repeatedly squeezing the lever handle 46, the plunger rod 32 can be rapidly advanced to force substantially large amounts of cement out of the cement cartridge 16.

However, as has been discussed, it is desirable to be able to slowly and precisely advance plunger rod 32 so that an exact and known amount of cement will be ejected from the container 16. To this end, the apparatus of this invention further includes a pair of attaching rods 80 and 81 having ends 82 and 83, respectively, that freely slide through apertures 84 and 85 of back wall 28. Ends 86 and 87 of rods 80 and 81, respectively, are securely attached to nut plate 88. Nut plate 88 includes a threaded portion 90 through which a threaded rod 92 passes. Threaded rod 92 has a first end pivotally secured to a pressure plate 94. The other end of threaded rod 92 has a wingscrew or knob 96 (preferably a knurled knob) secured thereto such that rotation of the knob will result in rotation of the threaded rod 92. Thus, rotation of knob 96 in a selected direction will cause movement of the threaded rod 92 in a first direction. Whereas, rotation of knob 96 in the opposite direction will cause movement of the threaded rod in the opposite direction. It will be appreciated, of course, that the amount of movement of threaded rod 92 resulting from rotation of knob 96 will depend upon the pitch of the threads of the threaded rod 92. Thus, the increments of motion can be readily adjusted by selecting the pitch of the threads. For purposes of monitoring the rotation of threaded rod 92, there is included an indexing mark 97 on knob 96. As shown, pressure plate 94 bears against pressure pad 37 such that motion of threaded rod 92 will result in motion of the plunger rod 32 and consequently motion of the cartridge piston 36, which will cause cement to be ejected from cartridge or container 16.

To allow for quick adjustment of the pressure plate 94 against the pressure pad 37, there is also included with the apparatus a second locking/quick-release lever mechanism 98. Locking/quick-release mechanism 98 operates the same as the locking/quick-release lever 66 of plunger rod advancing mechanism 30 and cooperates to grip rod 81 such that it cannot move in a rearward direction. It will be appreciated, of course, that a second similar locking mechanism 98A shown in dashed lines could be attached to back wall 28 for purposes of gripping rod 80.

Thus, in operation it is not necessary to attach the threaded rod 92 and knob 96 apparatus until after large amounts of cement have been ejected into the bone cavity by means of the lever handle mechanism 46. Then, the threaded rod 92 and knob 96 apparatus may be attached by passing the two parallel rods 80 and 81 through the apertures 84 and 85 and the locking/quick release mechanism 98 such that very small and precise amounts of cement may be ejected by use of the threaded rod 92 and knob 96 apparatus. This is accomplished by sliding rods 80 and 81 forward through apertures 84 and 85 until pressure plate 94 bears against pressure pad 36. It will of course be appreciated that once the rods 80 and 81 are moved forward, the locking/quick-release lever 98 will prevent them from moving in a rearward direction. Thus by exact rotation of knob 96, the plunger rod 32 may be moved forward by very accurate incremental distances.

The apparatus 110 of FIG. 4 is similar to the apparatus described in commonly owned U.S. Pat. No. 5,047,061, which is incorporated herein by reference in its entirety. Apparatus 110 includes a base guide 111, which is generally U-shaped and is described in detail in the above-referenced commonly owned patent. It includes orifices such as those shown at 112–114 in which drill bit sleeves (not shown) are inserted. Also within base guide 111 are four drilled and tapped apertures that are positioned for registration with aligned apertures in ceiling halves 121 and 122. Ceiling halves 121 and 122 are removably joined along line 123 and bolted together by two threaded fastening members, such as fastening member 124. The second fastening member is similar and is hidden from view. Four triple threaded bolts, such as 117 and 118 are provided for completing the fastening together of the parts in tight assembly.

In addition to the above-described parts, there is a separator sealer 126 that seals the bone cavity in a substantially fluid-tight manner. Sealer 126 is preferably constructed of a plastic which is pliable to a moderate degree or may be made of a silicone elastomer. As used herein, the word "plastic" in relation to sealer 126 is inclusive of any of the foregoing materials.

A femoral stem prosthesis as shown in U.S. Pat. No. 5,047,061 has a neck that extends upwardly through an opening between ceiling half 121 and mating half 122. The neck is surrounded by a holding unit 128 and thence downwardly through an opening in separator sealer 126. Two threaded orifices (not shown) in ceiling half 122 are provided for the temporary attachment of a syringe or cement ratchet gun mechanism for the injection of prosthesis cementing material and for providing a sensor orifice during initial pressurization. It will be noted that these orifices are closely adjacent each other. This is because the physicians are cutting off the head and neck of the femur much higher resulting in a smaller circle of ellipse in which to place the inlet and outlet valves. Therefore, the orifices are reduced in size and close together. Of course, they could be moved apart as far as necessary so long as they are both in fluid communication with the bone cavity.

The apparatus 110 can, of course, be used for inserting a prosthesis in the femoral canal of either leg of a person. In such case, if the person is lying on the left side and the prosthesis is to be inserted in the right femur, the apparatus 110 is placed on the femur so that the two orifices in ceiling half 122 are positioned one above the other and, in like manner, three additional orifices (not shown) in ceiling half 122 are also positioned one above the other. The cement then is injected into the bone cavity section through the lower one of the two orifices in ceiling half 122 and the sensor 151 (shown in FIG. 4) is inserted in the upper one of the first two orifices. The three orifices in half 121 are used for receiving a second sensor 157 (shown in FIG. 4). The uppermost one will be used for the second sensor 157. A needle, either 14 or 16 gauge, may be inserted through the uppermost orifice, for instance, and through the pliable separator sealer 126 thus forming an orifice therein, and a sensor tube 157, described earlier, can then be inserted in the orifice through the orifice in the sealer 126 and into the bone cavity.

The side view of the apparatus is shown attached to a femur section 141. The entire assembled apparatus can be designated "a sealing means". The prosthesis 139 has been attached to the apparatus as described in U.S. Pat. No. 5,047,061. A plug 138 is placed at the bottom of the bone section cavity or femoral canal 140. The base guide 111 is attached to the femur 141 and the ceiling halves 121 and 122 joined along line 123 by bolt 124 are attached to the base guide 111. The holding unit 128 extends upwardly through the ceiling halves 121 and 122 holding the top 148 of the prosthesis 139. Inlet valve 149 is placed in one of the orifices 131 or 132, depending upon the need as described earlier. It has a quick-disconnect 150 to which is attached the quick disconnect 24 of nozzle 20 of the cement gun or syringe. In the example shown in FIG. 4, the inlet valve 149 is placed in the lower orifice and a sensor 151 is placed in the upper orifice. A second sensor 157 is placed in the orifice in ceiling half 121.

The sensor device has a hollow cylinder and a threaded outer surface portion for insertion in either of the upper or lower threaded orifices in ceiling half 122. It also has a hollow sensor tube 151 (as shown in FIG. 4) with a smaller outer diameter than the inside diameter of the hollow cylinder. Epoxy or some other well-known material is used to hold the hollow sensor tube 151 in rigid relationship to the hollow cylinder and prevent cement from passing through the sensor device except through hollow sensor tube 151. The hollow sensor tube 151 may be approximately 2 cm in length and have an inside diameter in the range of about 0.062 inches to about 0.080 inches. This inside diameter is larger than the diameter of the intertrabecular spaces or Haversian canals in the cortical wall of the femur. Thus, any cement extruding from the femoral canal, or bone cavity, will extrude through the sensor 151 before it would pass through the intertrabecular spaces. This allows the physician to observe the viscosity of the extruded cement. If the cement is "runny" or spreads downwardly and outwardly from the sensor 151, the cement has low viscosity and must be allowed to mature further, become more doughy, before pressure is again applied. Thus, "controlled quantities" of cement can be extruded from the sensor because of its inside diameter. It is of great importance to be able to recognize that with the first pressurization that the cement is not of marginal viscosity such as that of a "free flowing liquid".

A "large orifice", as it is now used to allow air and body fluids to escape, allows a large amount of cement to "freely" extrude through the orifice with such a large diameter that the cement appears en masse as a glob which is slow in developing characteristics which could enable one to readily detect the difference from "free flowing" liquid and low to slightly moderately viscous cement.

For example, liquid material which is being extruded through a small diameter orifice such as that provided by hollow sensor tube 151 can easily be perceived as a liquid by its "free flow". Material of slight to moderate viscosity, on the other hand, will extrude from the tip of the orifice as a cylindrical column and maintain its columnar column shape for a short distance and then bend. The inside diameter of the novel sensor tube, although larger than the intertrabecular spaces, is small enough to allow cement to be extruded therefrom under safe pressure buildup in the bone cavity section.

It should be noted that the securing means, such as epoxy, attaches the hollow sensor tube 151 to the inside of the hollow cylinder in an eccentric relationship. This allows the hollow cylinder to be rotated in the chosen orifice to move the hollow sensor tube 151 to its furthest position to the adjacent orifice. Thus the hollow sensor tube 151 can be positioned in any desired circular relationship within the upper or lower orifice so that it can be adjusted to fit a bone cavity section of varying diameter to keep the sensor 151 as far from the injection orifice as possible to prevent it from becoming plugged with cement.

Injection valve 149 has a threaded end 154 that can be threadedly engaged with either of the lower or upper orifices. It also has a quick-disconnect valve 150 that allow the quick-disconnect end 24 of the cement gun of this invention to be quickly attached to and detached from the injection valve 149. It also has a threaded plunger 155 that can be used to force all of the cement out of the injection valve 149.

The present invention in cooperation with the sensor system of copending application Ser. No. 09/169,737 now U.S. Pat. No. 5,951,563 operates as follows. The bone cavity section is partially filled with flowable cement according to any presently available method to such a level that insertion of the prosthesis in the bone cavity section will not cause the cement level to rise to the top of the bone cavity section. The prosthesis is then attached to the apparatus 110 illustrated in FIG. 4 and the prosthesis is inserted in the bone cavity with the sealing device enclosing the bone cavity section in a fluid-tight manner. Cement is injected into the bone cavity section under pressure at cyclical intervals until the cement as set. First, when using the apparatus of FIGS. 1–3, the cement is injected into the bone cavity under pressure until a bead of cement is extruded from either the first sensor tube 151 or the second sensor 157. Should the first sensor tube 151 become covered with cement, the more remotely positioned second sensor 157 will exude air and body fluids until the cement has totally filled the bone cavity section. Then it will exude from one of the two sensors 151, 157 where it can be checked by the physician for its viscosity. Since there are two upper and lower spaced input orifices in ceiling half 122 and three spaced orifices in ceiling half 121 that can be used for a second sensor tube 157, the device allows a physician to use it when replacing a hip on either the right or the left side as described earlier. The appropriate ports or orifices can then be selected.

It will be appreciated by those skilled in the art that the cement cartridge of a ratchet gun may vary in diameter. For example, two readily available ratchet guns and corresponding cartridges have diameters of 1.3437 inches and 1.5 inches, respectively. Thus, a complete turn of the threaded rod 92 having a selected pitch of its threads will result in different quantities of cement being injected into the bone cavity. As an example only, one prototype of the present invention resulted in 4.88 cc being injected when used with a cement cartridge having a piston diameter of 1.5 inches. Therefore, to produce ¾" columns of cement from the orifice with this prototype, it was necessary to turn the knob by ⅓ of a turn. For embodiments of the invention having a different cartridge diameter or thread pitch of the threaded rod 92, it is important for the operator (surgeon) to know the amount of cement that will be ejected with one complete turn so as to estimate how much of a rotation or turn is necessary to eject the proper amount for a given pressurization.

FIG. 5 is a graph of pressure versus time illustrating the principle of the present invention. It is not intended to be exact, but is an example only to illustrate the principle. As can be seen in FIG. 5, the linear line 160 indicates that with increasing time it takes ever-increasing pressure to force the cement through the intertrabecular spaces because the cement is becoming more and more viscous. Clearly, then, when the cement is the least viscous, as shown during the first 3½ minutes, the pressure that is applied should be a minimum to keep from forcing the cement through the intertrabecular spaces.

The time scale actually begins with the time from beginning to mix the cement. Thus, after the cement has been mixed and inserted into the bone cavity section, there is an area 162 with a small amount of pressure generated inside the bone cavity. At 3½ minutes after mixing and with the bone cavity being filled with cement to a point below the top of the bone section, the prosthesis is inserted at 164 and the insertion increases the pressure within the canal. Then by waiting until 4½ minutes after mixing of the cement, additional cement is injected by the apparatus of this invention by use of the hand lever 46 such that the pressure at 166 is increased to a point at 168 until a cement bead 1½ to 1¾ inches long has been extruded from the flow sensor. All pressure is then released by removing the pressure on the cement being injected by depressing locking/quick-release lever 66. Tests have shown that the pressure on the cement will have reached approximately 25 psi and releasing the pressure will drop the pressure in the canal to under 10 psi as shown at 170 of FIG. 5. Of course, if the cement stops flowing from the sensor at any time during this process when cement is being added, one must assess whether the plug at the distal end is leaking, the seal between the apparatus and the cortex is leaking, or there is a hole or break in the femoral canal. If none of the three possibilities exists, then the cement is maturing much faster than usual and cement must be added until a bead 3½ to 4 inches long has been extruded and then immediately close the inlet valve.

Otherwise, at approximately 5½ minutes from the initial mixing of the cement, pressure plate 94 connected to threaded rod 92 is moved forward to bear on pressure pad 37 such that contact pad 34 can apply force to cartridge piston 36 and pressurized cement is added again to the bone cavity by precise rotation of knob 96, such as, for example, one-third turn or more, until a second bead 1 to 1½ inches long has been extruded. Then pressure is gradually released by rotating knob 96 in the opposite direction until the cement stops flowing from the sensor. This time, the pressure will have reached approximately the 34 or 35 psi as shown as 172. The pressure will then fall and remain as shown as 174.

At about 6½ minutes after mixing the cement, add pressure by rotating knob 96 so as to extrude a ½ to ¾ inch bead of cement. Usually the cement from the sensor at this time will stop flowing when one stops adding cement. Therefore, a release of the gun pressure may not be necessary. The pressure will be approximately 40 psi as shown at 176. The threaded piston in inlet valve is then moved inwardly to clear the cement from the injection valve, which adds approximately 1½ to 1¾ cc of cement to the femoral canal causing the pressure to rise to approximately 50 psi as shown at 178.

Pressuring cement to even greater pressures may improve the quality of the mature cement; however, there is evidence that indicates that pressurization which is greater than 60 psi probably has little or no effect in improving the quality of the cement or of improving fixation.

The present invention could be used to initially fill the femoral canal with cement before the prosthetic stem is inserted. A sealer could be used to seal the bone cavity. One orifice can be used to inject cement into the sealed cavity while the sensor, in a second orifice, provides the physician the necessary indication of cement viscosity as previously explained.

It will be noted that the procedure still requires the judgment and skill of the physician but, with the pressure of a suitable sensor such as disclosed in copending application Ser. No. 09/169,737, the physician knows the viscosity of the cement in the bone cavity and can then by use of the present invention make appropriate adjustments in pressure by precise rotation of knob 96 to get the maximum compression of the cement in the bone cavity while maintaining a pressure that will not force the cement through the cortical walls of the bone cavity.

Thus, there has been disclosed an apparatus for allowing a physician to inject precise amounts of cement to control the resulting pressure for cementing a prosthesis in a bone cavity section having a wall with intertrabecular spaces and/or Haversian canals. The bone cavity section is enclosed with a sealing means in a substantially fluid-tight fashion. Flowable cement is precisely injected in a first orifice in the sealing means by the apparatus of this invention in fluid communication with the bone cavity section. At least one sensor is provided in the sealing means in a second orifice adjacent the first orifice and in fluid communication with the bone cavity section. The sensor has a hollow tube mounted therein and has an inside diameter larger than the intertrabecular spaces so as to allow pressurized cement in the bone cavity section to always extrude through the hollow tube before passing through the intertrabecular spaces. The inside diameter of the tube is sufficiently small to allow the extrusion of controlled quantities of cement from the bone cavity section during pressurization to enable a physician to observe the cement flow viscosity as it extrudes from the hollow tube and thus enable the physician to precisely regulate the amount of pressure to be applied to the bone cavity by controlled rotation of the knob to compact the cement in the bone cavity section without forcing the cement through the intertrabecular spaces.

The corresponding structures, materials, acts, and equivalents of all means or step plus function elements in the claims below are intended to include any structure, material, or act for performing the function in combination with other claimed elements as specifically claimed.

What is claimed is:

1. A ratchet gun for forcing flowable cement out of a container having a moveable piston into a bone cavity under pressure, the ratchet gun comprising:

a first pressurization device including a plunger rod having a first and second end, said first end for bearing against the piston of said container and forcing said flowable cement from said container into said bone cavity in first increments; and a second pressurization device for bearing against said second end of said plunger rod to move said plunger rod and said piston of said container so as to force said flowable cement out of said container into said bone cavity in second increments smaller than said first increments to control the pressure in said bone cavity by causing it to increase in smaller increments than with said first pressurization device.

2. The ratchet gun of claim 1 wherein said first pressurization device comprises:

a frame;

a forward area of said frame for holding said container of cement;

a back area of said frame for supporting a plunger rod having first and second ends;

a contact pad connected to said first end of said plunger rod for engaging said piston of said container of cement to force cement from said container in said bone cavity; and a handle having a first section and a movable section pivotally coupled to said fixed section, said movable section being coupled to said plunger rod such that when said movable section of said handle is activated or squeezed, said plunger rod engages and moves said piston of said container of cement to force cement therefrom.

3. The ratchet gun of claim 2 and further comprising a locking/quick-release mechanism attached to said handle for readily allowing said plunger rod to advance said contact pad against said piston of said cement container to inject cement into said bone cavity and selectively allowing said plunger rod to move said contact pad away from said container to release pressure on said piston of said container.

4. The ratchet gun of claim 2 wherein said second end of said plunger rod includes a pressure pad and said second pressurization device includes:

a threaded rod having a pressure plate attached to a first end and a knob for rotating said threaded rod attached to a second end; and a support structure for supporting a plate spaced from said pressure pad, said plate including cooperating threads for supporting said threaded rod substantially coaxial with said plunger rod such that said pressure plate connected to said threaded rod is in contact with said pressure pad of said plunger rod such that rotation of said threaded rod will advance said plunger rod and said piston of said container and force flowable cement from said container.

5. The ratchet gun of claim 4 wherein said structure for supporting said plate comprises first and second rods each having first ends secured to said plate and second ends supported by said back area of said frame.

6. The ratchet gun of claim 5 wherein said back area defines first and second apertures for receiving said second ends of said first and second rods and further comprising a locking mechanism attached to said back area of said frame for securing at least said first rod to prevent movement of said nut plate in an axial direction away from said pressure pad of said plunger rod during advancement of said threaded rod toward said pressure pad.

7. The ratchet gun of claim 6 wherein said locking mechanism is a locking/quick-release mechanism which readily allows said first rod to move through its corresponding aperture to move said nut plate toward said pressure pad of said plunger rod and selectively allows said rod to move said nut plate away from said pressure pad of said plunger rod to release pressure on said piston of said container.

8. The ratchet gun of claim 4 and further comprising an index mark on said knob attached to said threaded rod such that an indication of rotation can be determined.

9. The ratchet gun of claim 6 and further comprising a second locking mechanism attached to said back area of said frame for securing said second rod to prevent movement of said nut plate in an axial direction away from said pressure pad of said plunger rod during advancement of said threaded rod toward said pressure pad.

10. The ratchet gun of claim 1 wherein said first pressurization device comprises:

a frame;

a forward area on said frame for holding said container of cement;

a back area of said frame for supporting a plunger rod having first and second ends;

a contact pad connected to said first end of said plunger rod for engaging said piston of said cement to force cement from said container in said bone cavity and a pressure pad connected to said second end;

advancing mechanism coupled to said plunger rod such that said plunger rod bears against and is engaged to move said piston of said container of cement;

said second pressurization device comprising a threaded rod having a pressure plate attached to a front end and a knob for rotating said threaded rod attached to a second end; and a support structure for supporting a nut plate spaced from said pressure pad, said nut plate supporting said threaded rod substantially coaxial with said plunger rod and such that said pressure plate of said threaded rod is in contact with said pressure pad of said plunger rod such that rotation of said threaded rod will advance said plunger rod in said piston of said container and force flowable cement from said container.

11. The ratchet gun of claim 10 further comprising a locking/quick-release means attached to said advancing mechanism for readily allowing said plunger rod to advance said contact pad against said piston of said cement container to inject cement into said bone cavity and selectively allow said plunger rod to move said contact pad away from said container to release pressure on said piston of said container.

12. The ratchet gun of claim 10 wherein said structure for supporting said nut plate comprises first and second rods, each having first ends secured to said nut plate and second ends secured to said back area of said frame.

13. The ratchet gun of claim 12 wherein said back area defines first and second apertures for receiving said second ends of said first and second rods and further comprises a locking mechanism attached to said back area of said frame for securing at least said first rod to prevent movement of said nut plate in an axial direction away from said second end of said plunger rod during advancement of said threaded rod toward said plunger rod to eject cement from said container.

14. The ratchet gun of claim 13 wherein said locking mechanism is a locking/quick-release mechanism which readily allows said first rod to move through its corresponding aperture to move said nut plate toward said second end of said plunger rod and selectively allows said rod to move said nut plate away from said second end of said plunger rod to release pressure on said piston of said container.

15. The ratchet gun of claim 10 and further comprising an index mark on said knob such that rotation of said knob can be determined.

16. An attachment for a ratchet gun having a movable plunger rod that moves a piston within a container of bone cement so as to pressurize bone cement in a bone cavity, said plunger rod extending between first and second ends, the first end of said plunger rod for engaging said piston within said container of cement, a pivotal handle engaging said plunger rod for moving said piston within said container in first increments to force said cement out of said container into said bone cavity under pressure, said attachment for bearing against said second end of said plunger rod to move said plunger rod and said piston within said container in second increments smaller than said first increments so as to enable a user to apply cement under pressure to said bone cavity in smaller units of pressure than with said pivotal handle.

17. The attachment of claim 16 wherein said second end of said piston includes:

a pressure pad and said attachment further comprises a threaded rod having a pressure plate attached to a front end and a knob for rotating said threaded rod attached to a second end; and a support structure for supporting a plate having cooperating threads and spaced from said pressure pad, said nut supporting said threaded rod substantially coaxial with said plunger rod such that said pressure plate is in contact with said pressure pad of said plunger rod and rotation of said threaded rod will advance said plunger rod and said piston and force flowable cement from said container.

18. The attachment of claim 17 and further including:

said support structure defining a pair of apertures for receiving first and second rods, respectively;

first and second rods each having first ends secured to said nut plate and at least said first rod having said second end secured to said support structure; and a locking mechanism attached to said support structure for securing said first rod to prevent movement of said nut plate in an axial direction away from said pressure pad of said piston during advancement of said threaded rod toward said piston to eject cement from said container.

19. The ratchet gun of claim 1 wherein said cooperating threads are defined in a nut member permanently attached to said back plate.

20. The ratchet gun of claim 1 wherein said cooperating threads are defined in a threaded portion of said back plate.

* * * * *